United States Patent [19]

Markovitz et al.

[11] Patent Number: 4,590,159
[45] Date of Patent: May 20, 1986

[54] ENHANCEMENT OF EXPRESSION OF PROTEIN SYNTHESIS IN *E. COLI*

[75] Inventors: Alvin Markovitz, Chicago, Ill.; Barbara A. Zehnbauer, Madison, Wis.; Joyce M. Schoemaker, Chicago, Ill.; Marc F. Charette, Wollaston, Mass.

[73] Assignee: University Patents, Inc., Westport, Conn.

[21] Appl. No.: 523,904

[22] Filed: Aug. 17, 1983

Related U.S. Application Data

[63] Continuation of Ser. No. 295,121, Aug. 21, 1981.

[51] Int. Cl.$^4$ .................. C12P 21/00; C12N 15/00
[52] U.S. Cl. ........................ 435/68; 435/172.3; 435/172.1; 935/38; 935/39; 935/10
[58] Field of Search .............. 435/68, 172.3, 172.1, 435/10, 38, 39

[56] References Cited

PUBLICATIONS

Gayda et al., Molec. Gen. Genet. 175, 325–332 (1979).
Chan et al., Proc. Natl. Acad. Sci. USA, vol. 76, No. 10, pp. 5036–5040 (Oct. 1979).
Shineberg et al., J. Bact., vol. 116, No. 3, pp. 1469–1471 (Dec. 1973).
Markovitz, Proc. Natl. Acad. Sci. USA, vol. 51, No. 2, pp. 239–246 (Feb. 1964).
Markovitz, et al., J. Bact., vol. 94, No. 2, pp. 388–395 (Aug. 1967).
Sutherland, Brochem. J. 115, 935 (1969).
Rubenstein et al., Diabetes, vol. 19, No. 8, pp. 546–552 (Aug. 1970).
Adler et al., J. Bact., vol. 87, No. 3, pp. 720–726 (Mar. 1964).
Takano, Proc. Natl. Acad. Sci. USA, vol. 68, No. 7, pp. 1469–1473 (Jul. 1971).
Gottesman et al., Cell, vol. 24, 225–233 (Apr. 1981).
Markovitz et al., Proc. Natl. Acad. Sci. USA, vol. 54, No. 4, pp. 1084–1091 (Oct. 1965).
Zehnbauer et al., Proc. Natl. Acad. Sci. USA, vol. 78, No. 4, pp. 2043–2047, Apr. 1981.
Walker et al., Molec. Gen. Genetics 108, 249–257 (1970).
Cheng et al., J. Bact., vol. 140, No. 1 (pp. 125–130) (Oct. 1979).
Flanders et al., Genetics 49: 237–246 (Feb. 1964).
Brukhani et al., Nature New Biology, vol. 243, pp. 238–241 (Jun. 20, 1973).
Markovitz, Surface Carbohydrates of the Prokaryotic Cell, Academic Press, pp. 415–462 (1977).
Goeddel et al., Proc. Natl. Acad. Sci USA, vol. 76, No. 1, pp. 106–110 (Jan. 1979).
Avni et al., J. Bact., vol. 129, No. 1, pp. 358–366 (Jan. 1977).
Gayda et al., J. Bact., vol. 127, No. 3, pp. 1208–1216 (Sep. 1976).
Gottesman et al., J. Bact., vol. 133, No. 2, pp. 844–851 (Feb. 1978).
Schoemaker et al., J. Bact., vol. 147, No. 1, pp. 46–56 (Jul. 1981).
Zehnbauer et al., J. Bact., vol. 143, No. 2, pp. 852–863 (Aug. 1980).
Goeddel et al., Nature, vol. 281, pp. 544–548, Oct. 18, 1979.

*Primary Examiner*—Alvin E. Tanenholtz
*Attorney, Agent, or Firm*—Barbara A. Shimei

[57] ABSTRACT

Endogenous and exogenous gene directed expression of protein synthesis in *Escherichia coli* is enhanced by transformation to incorporate a dominant mucoid mutant allele of the capR (lon) gene, preferably through use of the DNA plasmid, pBZ201M9 (A.T.C.C. Plasmid No. 40041) which carries the capR9 mutant allele.

12 Claims, No Drawings

ENHANCEMENT OF EXPRESSION OF PROTEIN SYNTHESIS IN E. COLI

This application is a continuation of application Ser. No. 295,121, filed Aug. 21, 1981.

BACKGROUND

The present invention relates generally to genetic engineering and more specifically to use of recombinant DNA techniques to secure expression of protein synthesis in selected unicellular organisms.

For many years, microorganisms have provided a source of commercially significant products such as antibiotics, enzymes and other biologically active proteins, alcohols and the like. Bacteria and yeasts have been the subject of intensive research effort which has had as its goal the enhancement of the cellular and extracellular yield of such commercial products by naturally-occurring and artificially mutated (e.g., radiation treated) strains of organisms. While manipulation of fermentation and product harvesting process parameters can frequently bring about dramatic increases in product yield for selected strains, it is most frequently the case that no degree of modification of culture and isolation conditions will result in enhancing an organism's "expression" of a particular product as evidenced by increased product yields.

A focus of genetic engineering in the recent past has been the use of recombinant DNA methodologies for the purification and amplification of genetic material. U.S. Pat. No. 4,237,224 to Cohen, et al., for example, relates to transformation of procaryotic unicellular host organisms with "hybrid" viral or circular plasmid DNA which includes exogenous DNA sequences. The procedures of the Cohen, et al. patent first involve manufacture of a transformation vector by enzymatically cleaving viral or circular plasmid DNA to form linear DNA strands. Selected foreign DNA strands are also prepared in linear form through use of similar enzymes. The linear viral or plasmid DNA is incubated with the foreign DNA in the presence of ligating enzymes capable of effecting a restoration process, and "hybrids" are formed which include the selected foreign DNA segment "spliced" into the viral or circular DNA plasmid. Transformation of compatible host unicellular organisms with the hybrid vector and propagation of transformant cells results in the formation of multiple copies of the foreign DNA in the host cell population. In some instances, the desired result is simply the amplification of the foreign DNA and the "product" harvested is DNA. More frequently, the goal of transformation is the expression by the host cells of the foreign DNA in the form of large scale synthesis of isolatable quantities of, e.g., commercially significant protein and polypeptide fragments coded for by the foreign DNA.

The success of procedures such as described by Cohen, et al. is due in large part to the ready availability of restriction endonuclease enzymes which facilitate the site-specific cleavage of both the unhybridized DNA vector and, e.g., eukaryotic DNA strands containing the foreign sequences of interest. Cleavage in a manner providing for the formation of complementary "ends" on the linear DNA strands greatly enhances the likelihood of functional incorporation of the foreign DNA into the reconstituted vector formed by ligating enzyme treatment. Verification of hybrid formation is facilitated by chromatographic techniques which can, for example, distinguish hybrid plasmids from non-hybrids on the basis of molecular weight. Other useful verification techniques involve radioactive DNA hybridization.

Another manipulative "tool" largely responsible for successes in transformation of procaryotic cells is the use of selectable "marker" gene sequences. Briefly put, hybrid vectors are employed which contain, in addition to the desired foreign DNA, one or more DNA sequences which code for expression of a phenotypic trait capable of distinguishing transformed from non-transformed host cells. Typical marker gene sequences are those which allow a transformed procaryotic cell to survive and propagate in a culture medium containing metals, antibiotics, and like components which would kill or severely inhibit propagation of non-transformed host cells.

Reports abound concerning successful transformation of host microorganisms such as *Escherichia coli* with common circular DNA plasmids such as pBR322 which has been hybridized to incorporate exogenous procaryotic or eukaryotic genes. Relatively large quantities of the protein products coded for by the foreign genes can often be isolated from the transformant cells or from the culture medium in which the cells are propagated.

Rather expectedly, the literature provides few details of the numerous unsuccessful attempts at securing desired expression of foreign gene directed protein synthesis using standard host/vector methodologies. While in some instances transformation "failures" are simply the result of defective hybrid formation, it is nonetheless frequently the case that an "unsuccessful" vector is verified as including all portions of a foreign gene sequence that are otherwise necessary for directing synthesis of the desired protein product. Similarly, the lack of success in some experiments can be attributed to a generalized incompatibility between host and vector. In many cases, however, stable incorporation of the vector (accompanied by extensive replication and expression of marker gene phenotype) does take place, but expression of desired protein synthesis does not.

The failure of host microorganisms to express proteins coded for by foreign DNA sequences may also be a problem in recombinant DNA methodologies involving direct incorporation of exogenous DNA into chromosomes of microorganisms. While chromatographic and radioisotopic DNA hybridization studies might verify incorporation of entire genes (including necessary promoter and leader sequences) into host genomes, there may be no corresponding expression of the protein coded for by the gene.

Among the hypotheses advanced in explanation for the failure of otherwise fully operational transformation systems to provide the desired yields of exogenous gene directed protein are: (1) interference by host cell constituents in transcription and/or translation of the foreign DNA; and (2) interference by host cell constituents in the accumulation of readily isolatable quantities of gene products in the host cells.

As indicated by the above, therefore, there exists a general need in the art for methods and materials which will serve to enhance the expression of endogenous gene directed protein synthesis in naturally occurring and mutant microorganisms as well as expression of exogenous gene directed protein synthesis in microorganisms which have been the subject of transformations with exogenous DNA by recombinant DNA methodologies.

BRIEF SUMMARY

According to the present invention, endogenous and exogenous gene directed expression of protein synthesis by *Escherichia coli* cells is enhanced by transformation of the cells to incorporate one or more copies of a dominant mucoid mutant allele of capR (lon) gene, preferably the capR9 allele. The mutant capR9 allele is publicly available as a component of the DNA plasmid, pBZ201M9 (A.T.C.C. Plasmid No. 40041) which plasmid provides a presently preferred vehicle for effecting *E. coli* cell transformation according to the invention.

In one aspect of the invention, the expression of protein synthesis by endogenous genes of naturally occurring and mutant *E. coli* strains is enhanced by the simple transformation of cells with an *E. coli* plasmid such as A.T.C.C. Plasmid No. 40041 which includes the capR9 allele. The same procedure is available to enhance expression of protein synthesis in *E. coli* strains which have had exogenous, protein synthesis directing, genes stably incorporated into chromosomes.

According to another aspect of the invention, *E. coli* strains which have been transformed with a first vector including a selected exogenous DNA sequence coding for a protein of interest are additionally transformed with a plasmid providing the capR9 allele such as A.T.C.C. Plasmid No. 40041. Further, the capR9 allele may be incorporated on the same hybrid vector as the selected exogenous DNA sequence and both genes (possibly under the control of the same promoter) may be simultaneously introduced into the *E. coli* host, with verification of the transformation secured through monitoring for a single marker gene.

Other aspects and advantages of the present invention will be apparent from the following detailed description.

DETAILED DESCRIPTION

As used herein, the term "protein" shall mean and include not only whole functional proteins, but also polypeptides. "Enhancement of expression" of protein synthesis shall designate increasing the net quantity of a selected protein isolatable from a system, whether such increase is attributable to an increase in the amount of the protein synthesized by cells in the system or to an increase in synthesized intact protein remaining available for harvesting from the system. As used herein, the term "genetically transforming" shall mean effecting the stable incorporation of a selected DNA sequence into an *E. coli* cell, whether by way of insertion into chromosomal DNA or by way of incorporation of a vector including the selected sequence.

The present invention has its origins, in part, in work commenced over fifteen years ago by co-inventor Markovitz and his co-workers. See, e.g., Markovitz, et al., P.N.A.S. 51, 239 (1964) and 54, 1084 (1965). Briefly stated, this work dealt with mutants of an *E. coli* K-12 regulator gene, "capR" (also referred to in the art as the "lon" gene) which controls the synthesis of capsular polysaccharide and the enzymes involved in capsular polysaccharide synthesis.

Cells containing certain dominant mutant forms of the capR gene were noted to display a distinct "mucoid" phenotype when grown on minimal medium. The mucoid appearance was determined to result from overproduction of capsular polysaccharide, which is composed of glucose, galactose, fucose, glucuronic acid, acetate, and pyruvate. [See, Sutherland, Biochem. J., 115, pp. 935–945 (1969).] The overproduction of capsular polysaccharide observed in capR mutants has been attributed to derepression of ten enzymes in at least four spatially separated operons concerned with production of the polysaccharide capsule. [See, Markovitz, at pp. 415–462 in *Surface Carbohydrates of the Procaryotic Cell* (Sutherland, ed.) Academic Press, New York (1977).]

Other mutant capR phenotypes include: failure to lysogenize temperate phages [Takano, *P.N.A.S.*, 68, pp. 1469–1473 (1971)]; increased sensitivity to radiation [Howard-Flanders, et al., *Genetics*, 49, pp. 237–246 (1964) and Adler, et al., *J.Bacteriol.*, 87, pp. 720–726 (1964)]; abnormal cell division [Walker, et al., *Mol.Gen.-Genet.*, 108, pp. 249–257 (1970) and Gayda, et al., *J.Bacteriol.*, 127, pp. 1208–1216 (1976)]; and reduced degradation of certain normal [Gayda, et al., *Mol.Gen.Genet.*, 175, pp. 325–332 (1979)] and abnormal proteins [Bukhari, et al., *Nature New Biol. (London)*, 243, pp. 238–241 (1973) and Shineberg, et al., *J.Bacteriol.*, 116, pp. 1469–1471 (1973)], as well as lambda viral protein [Gottesman, et al., *Cell*, 24, pp. 225–233 (1981)].

Studies of the mucoid phenotype indicate that overproduction of capsular polysaccharide involves derepression of the galETK operon and that the mucoid phenotype is not, by itself, responsible for other capR mutant phenotypes. Gal⁻ derivatives of capR mutants, for example, result in nonmucoid colonies that continue to exhibit the remaining capR mutant phenotypes. [See, e.g., Markovitz (1977) supra and Gottesman, et al., *J.Bacteriol.*, 133, pp. 844–851 (1978).

One particular dominant mucoid mutant allele of the capR gene, called capR9, is of special significance to the present invention. In a haploid state, capR9 strains exhibit all of the standard phenotypes (mucoid appearance, radiation sensitivity, etc.). However, in partial diploid studies when the capR9 allele was placed on a plasmid with the capR+ allele on the chromosome, the mutant (mucoid) phenotype was dominant to the wild type (nonmucoid) phenotype. See, e.g., Markovitz, et al., *P.N.A.S.*, 54, pp. 1084–1091 (1965) for discussion of the capR9 allele (referred to therein as C-9) as well as other dominant mutant mucoid alleles (referred to as C-62 and C-66). This mutant-phenotype dominance was reversed when the capR+ gene was on the plasmid and the capR9 mutation was on the chromosome. These results were interpreted as indicating that the capR (lon) gene product acts as an oligomer composed of identical subunits. According to this hypothesis, the capR9 gene would code for a defective subunit. When the capR9 was present in multiple copies (perhaps 2–3 times for an F' plasmid), the defective subunits would dominate in the oligomer and the mutant phenotype would be expressed. This would be reversed when the wild type is in multiple copies. It is believed that the capR9 allele codes for a shortened polypeptide product because its phenotypes are partially reversed by ochre (nonsense) suppressors [Markovitz, et al. *J.Bacteriol.*, 94, pp. 338–395 (1967) and Markovitz (1977) supra.]

EXAMPLE 1

An illustrative example of the methods of the invention which result in the enhanced expression of endogenous gene directed protein synthesis is provided in the publication of co-inventors Zehnbauer and Markovitz appearing in *J.Bacteriol.*, 143, pp. 852–863 (published Aug. 27, 1980).

Briefly summarized the method therein described involved use of *E. coli* strain CSR603 which displays the inability to repair damage to DNA from exposure to ultraviolet light. When the cells are transformed by plasmids which represent a smaller target for DNA damage and then irradiated with ultraviolet light, they are generally capable of expressing those proteins coded by the plasmid, but not by the chromosome. Test cells were transformed with both plasmid pBZ201 containing the wild type capR gene and pBZ201M9 which contained the capR9 mutation. The transformation procedure employed was as described in Avni, et al. *J.Bacteriol.*, 129, pp. 358-366 (1977). (DNA plasmid pBZ201M9 has been deposited by applicants with the American Type Culture Collection, 12301 Parklawn Drive, Rockville, M.N. 20852 and the plasmid has been assigned A.T.C.C. Plasmid No. 40041). Non-transformed (control) CSR603 cells together with cells transformed with plasmid pBZ201 and cells transformed with plasmid pBZ201M9 were all exposed to ultraviolet light. Radioactive labelled $^{35}$S-methionine was added to the culture medium containing the UV-treated cells and proteins harvested from the cells were thereafter subjected to electrophoretic analysis.

The control CSR603 cells showed no labelled proteins. Cells transformed with the wild type plasmid displayed two distinct proteins, one of which is characteristic of the wild type capR gene coded by the plasmid. CSR603 cells transformed with the capR9 plasmid displayed not only a labelled protein characteristic of the capR9 gene but also a wide array of unidentified cellular proteins not present in either the control CSR603 cells or those transformed with the pBZ201 plasmid.

EXAMPLE 2

An illustrative example of practice of the invention to effect enhanced expression of an exogenous gene is provided by the following description of work performed in collaboration with the inventors by Donald F. Steiner and Shu Jin Chan of the Department of Biochemistry of The University of Chicago.

*E. coli* K-12, strain JA221 ($r_K^- m_K^+$ derivative of strain C600 containing *trpAE5, leu-6, recA*) was transformed in the usual fashion to contain plasmid PEX2. Plasmid PEX2 is derived from plasmid pRI-11 which contains the rat proinsulin gene [Chan, et al., *P.N.A.S.*, 76, pp. 5036-5040 (1979)]. Plasmid PEX2 was engineered to contain the lac promoter DNA inserted into the appropriate position of pRI-11 so that expression of synthesis of rat proinsulin messenger RNA and protein should occur. Radioimmunoassay [Rubenstein, et al., *Diabetes*, 19, pp. 546-553 (1970)] for rat proinsulin product of cultured growth of the transformed cells detected no proinsulin product, although the assay procedure was capable of detecting as little as 0.5 nanograms per liter of culture.

The "unsuccessful" transformant cells were thereafter further transformed with the capR9 plasmid, pBZ201M9 (A.T.C.C. Plasmid No. 40041). Products of cells transformed with the capR9 allele were subjected to radioimmunoassay as above and revealed the presence of about 60 nanograms per liter of rat proinsulin which is the equivalent of approximately 100 molecules per cell.

While the first of the above two illustrative examples demonstrates operability of methods of the invention for enhancement of expression of endogenous gene directed protein synthesis in *E. coli* strains by transformation to incorporate plasmid pBZ201M9 (A.T.C.C. No. 40041), it will be apparent that any DNA plasmid or similar DNA vector (e.g., bacteriophage DNA, which is frequently referred to as plasmid DNA in the context of cell transformation) may be suitably fashioned to incorporate the capR9 gene or other dominant mucoid mutant allele of capR, and that the resulting hybrid may be employed in practice of the invention. Plasmids providing either more or fewer copies than pBZ201 in transformed cells may be used.

In a like manner, when a dominant mucoid mutant of the capsular polysaccharide, capR, gene such as capR9 is to be employed to enhance expression of protein synthesis in *E. coli* by an exogenous gene, numerous alternatives to the Example 2 procedure of effecting a first transformation with a plasmid incorporating the exogenous gene and a second transformation with a vector incorporating the capR9 gene exist. The mutant allele could be directly incorporated into the chromosome. A concurrent transformation of the *E. coli* host with both the selected exogenous gene and the capR9 gene could be made using a single hybrid vector incorporating both genes. DNA plasmid pBZ201M9 may itself be further hybridized, for example, to incorporate a selected exogenous gene coding for a protein of interest.

While both of the above examples relate to isolation of protein directly from *E. coli* cells, it is contemplated that harvesting of the protein product of interest may be from the culture medium in which transformed *E. coli* cells are propagated. Similarly, while both examples involve use of K-12 *E. coli* strains, the invention is equally applicable to other strains.

The precise mode of operation of, e.g., the capR9 gene, in enhancing expression of endogenous and exogenous gene directed protein synthesis is at present not fully elucidated. The proposed theories of operation noted below are therefore not intended to be limiting on the invention.

According to one theory of the invention, protein coded for by the dominant mucoid mutant gene functions to bind with and stabilize nucleic acids (specifically messenger RNA) in the host cell, preventing degradation and hence allowing for enhanced expression in the form of enhanced protein formation. Such a theory provides a reasonable explanation for the results obtained in Example 1 above. More particularly, the appearance of significant quantities of unidentified labelled protein in irradiated test cells could be due to the capR9 protein binding to m-RNA formed prior to irradiation (and chromosomal inactivation). The m-RNA so stabilized and protected from degradation would be available to operate as a translational template for synthesis of protein incorporating the labelled methionine.

An alternative theory of operation of the invention has as its basis the ability of the protein coded for by the mutant allele to diminish activity of the wild type capR protein in degrading such proteins formed by the host cell which may be recognized in the cell as "foreign". This theory provides an explanation for the remarkable results obtained in Example 2 above.

In the course of exhaustive analysis of the activities of the protein coded for by the wild type capR gene, it was determined that gene product activities included an ATP-hydrolysis-dependent protease activity, an ATPase activity associated with protease activity, (i.e., displayed in the presence of casein), and a second ATPase activity stimulated by DNA. See, e.g., Schoemaker, et al., *J.Bacteriol.*, 147, pp. 46-56 (1981) and Zehnbauer, et al., *P.N.A.S.*, 78, pp. 2043-2047 (1981).

The gene product of capR9, however, shows no ATP-dependent protease activity, practically no ATPase activity in the presence of casein, and greatly reduced DNA-dependent ATPase activity. In vitro experiments using mixtures of both capR and capR9 protein reveal significant diminution of wild type protein protease activity. Whether, in vivo, the mutant protein binds to (and represses activity of) the wild type protein or whether the putatively inactive mutant protein simply competes more effectively for binding sites than the wild type protein, the net result appears to be enhanced expression of certain proteins in the form of diminished degradation thereof by the protease products of the wild type capR gene.

Thus, whether the presence of the mutant gene and its products operates at the transcriptional or translational level to quantitatively enhance protein synthesis or operates in a protective fashion to block enzymatic degradation of proteins synthesized, the overall result is enhanced expression of protein synthesis in terms of greater net quantities of isolatable products of exogenous and endogenous gene directed protein synthesis.

The present invention additionally comprehends improvements in prior methods for securing production, in *E. coli* host cells, of protein coded for by exogenous genes, which improvements comprise employing *E. coli* host cells which contain a chromosomal mutation in the capsular polysaccharide, capR (lon), gene. While preferred methods involve use of *E. coli* cells having the above-noted dominant mucoid mutant allele (especially the capR9 allele), also comprehended is the use of cells carrying other capR mutations, including recessive mutations. An example of the practice of this improved methodology is provided by the following description of work performed by collaborators Donald F. Steiner and Shu Jin Chan on *E. coli* host cell strains which differed from each other, inter alia, in terms of the presence or absence of a putatatively recessive chromosomal mutation in the capR (lon) gene.

EXAMPLE 3

Parallel experiments were carried out according to Example 2 using as a transformation vector the PEX2 plasmid containing a rat proinsulin gene. In the first experiment the host was *E. coli* K-12, strain 3343 (*F−, thi, cys, lys, xyl, mtl, mal, strA, lacZ, ptr-3*). The *ptr-3* mutation is a mutation in a protease-directing gene other than capR [Cheng, et al , J. Bacteriol. 140, pp. 125-130 (1979)]. The host strain for the second experiment was *E. coli* K-12, strain 3325 [*F−, strA, nalA, lacZ, ptr-3, lon-rl* (also referred to as *deg-rl*). See, Gottesman, et al., *J.Bacteriol.*, 133, pp. 844–851 (1978)]. Radioimmunoassays for rat proinsulin were carried out according to the procedures noted in Example 2. No rat proinsulin production was detected in the host cells of the first experiment. Rat proinsulin was detected in the host cells of the second experiment, wherein the host strain carried a mutation in the capR (lon) gene.

Numerous modifications and variations in the practice of the invention as described above are expected to occur to those skilled in the art. Therefore, only such limitations as appear in the appended claims should be placed on the invention.

What is claimed is:

1. A method for enhancing expression of exogenous gene directed protein synthesis in *Escherichia coli* cells having an exogenous gene incorporated therein, said method comprising the step of genetically transforming the cells to incorporate a dominant mucoid mutant allele of the capsular polysaccharide, capR, gene which capR gene is expressed in the transformed cells.

2. A method according to claim 1 wherein said dominant mucoid mutant allele is the capR9 allele.

3. A method according to claim 1 wherein said transforming step comprises transformation with the DNA Plasmid pBZ201M9 (A.T.C.C. Plasmid No. 40041).

4. In the method for producing, in *Escherichia coli* cells, a protein coded for by a selected exogenous gene, the improvement comprising:
   (a) genetically transforming the cells to incorporate said selected exogenous gene;
   (b) genetically transforming the cells to incorporate a dominant mucoid mutant allele of the capsular polysaccharide, capR, gene;
   (c) propagating cells transformed according to steps (a) and (b); and
   (d) isolating protein coded for by said selected exogenous gene and produced by cells propagated according to step (c).

5. The improvement of claim 4 wherein said dominant mucoid mutant allele is the capR9 allele.

6. The improvement of claim 4 wherein step (b) is carried out using the DNA plasmid pBZ201M9 (A.T.C.C. Plasmid No. 40041).

7. The improvement of claim 4 wherein steps (a) and (b) are carried out using a single transformation vector including both said selected exogenous gene and said dominant mucoid mutant allele.

8. The improvement of claim 7 wherein said dominant mucoid mutant allele is the capR9 allele.

9. The improvement of claim 7 wherein said single transformation vector is DNA plasmid pBZ201M9 (A.T.C.C Plasmid No. 40041) which has been hybridized to include said selected exogenous gene.

10. A method for enhancing expression of endogenous gene directed protein synthesis in *Escherichia coli* cells, said method comprising the step of genetically transforming the cells to incorporate a plasmid comprising a dominant mucoid mutant allele of the capsular polysaccharide, capR, gene which capR gene is expressed in the transformed cells.

11. A method according to claim 10 wherein said dominant mucoid mutant allele is the capR9 allele.

12. A method according to claim 10, wherein said transforming step comprises transformation with the DNA Plasmid pBZ201M9 (A.T.C.C. Plasmid No. 40041).

* * * * *

UNITED STATES PATENT AND TRADEMARK OFFICE
CERTIFICATE OF CORRECTION

PATENT NO. : 4,590,159

DATED : 20 May 1986

INVENTOR(S) : Markovitz et al.

It is certified that error appears in the above-identified patent and that said Letters Patent is hereby corrected as shown below:

In Column 1, after line 6 and before "BACKGROUND", please insert the following paragraph:

--The invention described herein was made in the course of work partly supported by a grant from the National Institute of Health.--

Signed and Sealed this

Eleventh Day of December, 1990

*Attest:*

HARRY F. MANBECK, JR.

*Attesting Officer*      *Commissioner of Patents and Trademarks*